United States Patent
Corbera-Arjona et al.

(10) Patent No.: US 8,481,567 B2
(45) Date of Patent: *Jul. 9, 2013

(54) SIGMA RECEPTOR COMPOUNDS

(75) Inventors: Jordi Corbera-Arjona, Barcelona (ES); David Vano-Domenech, Barcelona (ES); Joerg Holenz, Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 325 days.

This patent is subject to a terminal disclaimer.

(21) Appl. No.: 12/281,300

(22) PCT Filed: Mar. 2, 2007

(86) PCT No.: PCT/EP2007/001825
§ 371 (c)(1),
(2), (4) Date: Jan. 29, 2009

(87) PCT Pub. No.: WO2007/098962
PCT Pub. Date: Sep. 7, 2007

(65) Prior Publication Data
US 2009/0197915 A1    Aug. 6, 2009

(30) Foreign Application Priority Data
Mar. 2, 2006    (EP) .................................. 06004287

(51) Int. Cl.
*A61K 31/445* (2006.01)

(52) U.S. Cl.
USPC ....................................................... 514/323

(58) Field of Classification Search
None
See application file for complete search history.

(56) References Cited

U.S. PATENT DOCUMENTS 7,282,499 B2 * 10/2007 Arjona et al. ............... 514/234.5
7,829,559 B2 * 11/2010 Corbera Arjona et al. 514/234.5

FOREIGN PATENT DOCUMENTS

| DE | 199 43 508 A1 | 3/2001 |
| EP | 1 634 873 A1 | 3/2006 |
| WO | WO 02/055517 | * 7/2002 |

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Thiel (Nature Biotechnol 2:513-519, 2004.*
Vangveroavong et al (Bioorg Med Chem 14:815-825, 2006).*
Williams et al (Foye's Principles of Medicinal Chemistry, 5th Edition, pp. 59-63, 2002).*
Anderson (Chem and Biol 10:787-797, 2003).*
Thiel (Nature Biotechnol 2:513-519, 2004).*
Maier et al (J Med Chem 45:4923-4930, 2002).*
International Search Report issued for PCT/EP2007/001825, mailed Jun. 20, 2007.
Berardi et al., "Novel Potent $\sigma_1$ Ligands: $N$-[ω-Tetralin-1-yl)alkyl]piperidine Derivatives," *Journal of Medicinal Chemistry*, 39:4255-4260 (1996).
Perrone et al., "High Affinity and Selectivity on 5-$HT_{1A}$ Receptor of 1-Aryl-4-[(1-tetralin)alkyl]piperazines. 2," *Journal of Medicinal Chemistry*, 38:942-949 (1995).

* cited by examiner

*Primary Examiner* — Craig Ricci
(74) *Attorney, Agent, or Firm* — Heslin Rothenberg Farley & Mesiti P.C.; Andrew K. Gonsalves

(57) ABSTRACT

The present invention relates to compounds of formula (I), methods for their preparation, medicaments comprising these compounds as well their use in the manufacture of a medicament for the treatment of humans and animals.

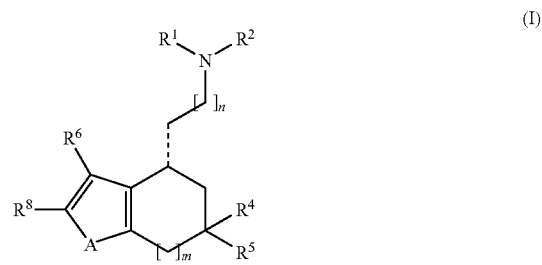

(I)

10 Claims, No Drawings

SIGMA RECEPTOR COMPOUNDS

CROSS REFERENCE TO RELATED APPLICATIONS

This application is a U.S. National Phase filing under 35 U.S.C. §371 of International Application PCT/EP2007/001825, filed Mar. 2, 2007, and published as WO 2007/098962 on Sep. 7, 2007. PCT/EP2007/001825 claimed benefit of priority from European Patent Application No. EP 0-600-4287.6, filed Mar. 2, 2006. The entire contents of each of the prior applications are incorporated herein by reference.

FIELD OF THE INVENTION

The present invention relates to compounds having pharmacological activity towards the sigma receptor, to processes of preparation of such compounds, to medicaments comprising them, and to their use in therapy and prophylaxis, in particular for the treatment of psychosis or pain.

BACKGROUND OF THE INVENTION

The search for new therapeutic agents has been greatly aided in recent years by better understanding of the structure of proteins and other biomolecules associated with target diseases. One important class of these proteins is the sigma receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF 10047, (+)-cyclazocine, and (+)-pentazocine and also for some narcoleptics such as haloperidol. The sigma receptor has at least two subtypes, which may be discriminated by stereoselective isomers of these pharmacoactive drugs. SKF 10047 has nanomolar affinity for the sigma-1 site, and has micromolar affinity for the sigma-2 site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International Patent Application No. WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom. The terms aryl and heteroaryl are defined by mention of a number of such substituents.

European patent publication No. EP 0 414 289 AI generically discloses a class of 1,2,3,4-tetrahydro-spiro[naphthalene-1,4'-piperidine] and 1,4-dihydro-spiro [naphthalene-1, 4'-piperidine] derivatives substituted at the piperidine N-atom with a hydrocarbon group alleged to have selective sigma receptor antagonistic activity. The term hydrocarbon, as defined in said patent, covers all possible straight chained, cyclic, heterocyclic, etc. groups. However, only compounds having benzyl, phenethyl, cycloalkylmethyl, furyl- or thienylmethyl or lower alkyl or alkenyl as the hydrocarbon substituent at the piperidine nitrogen atom are specifically disclosed. The compounds are stated to displace tritiated di-tolyl guanidine (DTG) from sigma sites with potencies better than 200 nM. As a particularly preferred compound is mentioned 1'-benzyl-1,2,3,4-tetrahydro-spiro[naphthalene-1,4'-piperidine].

European patent publication No. EP 0 445 974 A2 generically describes the corresponding spiro[indane-1,4'-piperidine] and spiro[benzocycloheptene-5,4'-piperidine] derivatives. Again the compounds are only stated to displace tritiated di-tolyl guanidine (DTG) from sigma sites with potencies better than 200 nM European patent Application No. EP 0 431 943 A2 relates to a further extremely broad class of spiropiperidine compounds substituted at the piperidine N-atom and claimed to be useful as antiarrhythmics and for impaired cardiac pump function. The said application exemplifies several compounds, the majority of which contain an oxo and/or a sulfonylamino substituent in the spiro cyclic ring system. Of the remainder compounds, the main part has another polar substituent attached to the spiro nucleus and/or they have some polar substituents in the substituent on the piperidine N-atom. No suggestion or indication of effect of the compounds on the sigma receptor is given.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of compounds which are particularly selective inhibitors of the sigma receptor. The compounds present a furan and/or a pyrrol ring which is condensed with a cycloalkyl ring having 5, 6 or 7 carbon atoms.

In one aspect the invention is directed to a compound of general formula (I),

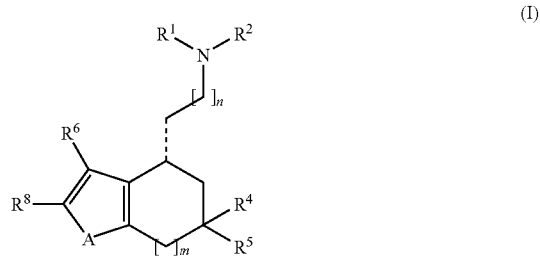

wherein
A represents a NR³ group or O;
m is selected from 0, 1, 2;
n is selected from 0, 1, 2, 3, 4;

the dotted line ------ represents either a single or a double bond;

$R^1$ and $R^2$, identical or different, represent a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system; a (C=O)—$R^7$ group; a (C=O)—O—$R^7$ group; a ($SO_t$)—$R^7$ group; a $NR^7R^{7a}$ group; a (C=O)—$NR^7R^{7a}$ group; an O—$R^7$ group; or form together with the bridging nitrogen atom an at least mono-cyclic, optionally at least mono-substituted, at least one heteroatom containing heterocyclyl group which is optionally condensed with an optionally at least mono-substituted mono- or polycyclic ring system and/or bonded via linear alkylen groups and/or is optionally bound through a spirocyclic binding to an optionally at least mono-substituted mono- or polycyclic ring system;

t is selected from 0, 1, 2 or 3;

$R^3$ represents a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system;

$R^4$ and $R^5$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group; or form together a 3 to 6-membered, optionally at least mono-substituted ring system;

$R^6$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^7$ and $R^{7a}$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^8$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferably t is selected from 1, 2 or 3.

In one embodiment the following proviso applies:

with the proviso that
    if A represents O;
    and n is selected from 0, 1, 2;
    $R^1$ and $R^2$ may not form, together with their bridging nitrogen atom, an imidazole group.

In one other embodiment the following proviso applies:
with the proviso that
if A represents O, m and n are each 1, $R^8$ is Methyl, and the dotted line ------ represents a double bond, $R^4$ and $R^5$ will both be hydrogen.

In one other embodiment the following proviso applies:
with the proviso that
if A represents $NR^3$ and $R^3$ is H, m and n are each 1, the dotted line ------ represents a single bond, $R^4$, $R^5$ and $R^6$ are hydrogen and $R^8$ is $CH_2OH$, $R^1$ and $R^2$ may not form together with the bridging nitrogen atom an unsubstituted pyrrolidine.

In one other embodiment the following proviso applies:
with the proviso that
if A represents $NR^3$ and $R^3$ is H, m and n are each 1, the dotted line ------ represents a single bond, $R^4$, $R^5$ and $R^6$ are hydrogen and $R^8$ is C(O)H, $R^1$ and $R^2$ may not form together with the bridging nitrogen atom an unsubstituted pyrrolidine.

In one other embodiment the following proviso applies:
with the proviso that
if A represents $NR^3$ and $R^3$ is H, m and n are each 1, the dotted line ------ represents a single bond and $R^4$, $R^5$, $R^6$ and $R^8$ are hydrogen, $R^1$ and $R^2$ may not form together with the bridging nitrogen atom an unsubstituted pyrrolidine;

In one other embodiment the following proviso applies:
with the proviso that
if A represents $NR^3$ and $R^3$ is H, m and n are each 1, $R^4$, $R^5$, $R^6$ are hydrogen, the dotted line ------ represents a single bond, and $R^1$ and $R^2$ form together with the bridging nitrogen atom an unsubstituted pyrrolidine, $R^8$ may not be CH=Het, with Het being a phenyl-substituted 1,3-dihydro-indol-2-one;

In one other embodiment the following proviso applies:
with the proviso that
if A represents $NR^3$ and $R^3$ is H, m is 1, n is 0, $R^4$, $R^5$, $R^6$ and $R^8$ are hydrogen, and the dotted line ------ represents a double bond, one of $R^1$ or $R^2$ may not be hydrogen, when the other is C(O)-cyclohexyl.

In one other embodiment the following proviso applies:
with the provisos that
if A represents $NR^3$ and $R^3$ is H, m and n are each 1, the dotted line ------ represents a single bond, $R^4$, $R^5$ and $R^6$ are hydrogen and $R^8$ is $CH_2OH$, $R^1$ and $R^2$ may not form together with the bridging nitrogen atom an unsubstituted pyrrolidine;
if A represents $NR^3$ and $R^3$ is H, m and n are each 1, the dotted line ------ represents a single bond, and $R^4$, $R^5$, $R^6$ and $R^8$ are hydrogen, $R^1$ and $R^2$ may not form together with the bridging nitrogen atom an unsubstituted pyrrolidine;
if A represents $NR^3$ and $R^3$ is H, m and n are each 1, $R^4$, $R^5$, $R^6$ are hydrogen, the dotted line ------ represents a single bond, and $R^1$ and $R^2$ form together with the bridging nitrogen atom an unsubstituted pyrrolidine, $R^8$ may not be CH=Het, with Het being a phenyl-substituted 1,3-dihydro-indol-2-one;
if A represents $NR^3$ and $R^3$ is H, m is 1, n is 0, $R^4$, $R^5$, $R^6$ and $R^8$ are hydrogen, and the dotted line ------ represents a double bond, one of $R^1$ or $R^2$ may not be hydrogen, when the other is C(O)-cyclohexyl;
if A represents O; and n is selected from 0, 1, 2; $R^1$ and $R^2$ may not form, together with their bridging nitrogen atom, an imidazole group;
if A represents O, m and n are each 1, $R^8$ is Methyl and the dotted line ------ represents a double bond, $R^4$ and $R^5$ will both be hydrogen.

In another aspect the invention is directed to a compound of general formula (I),

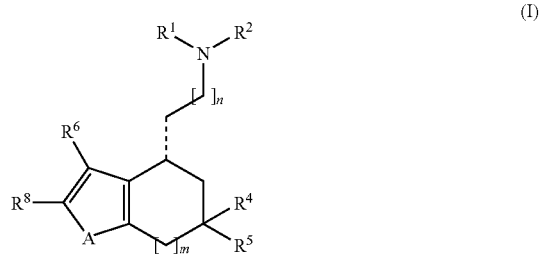

wherein
A represents an $NR^3$ group;
m is selected from 0, 1, 2;
n is selected from 0, 1, 2, 3, 4;
the dotted line ------ represents either a single or a double bond;
$R^1$ and $R^2$, identical or different, represent a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system; a (C=O)—$R^7$ group; a (C=O)—O—$R^7$ group; a $(SO_t)$—$R^7$ group; a $NR^7R^{7a}$ group; a (C=O)—$NR^7R^{7a}$ group; an O—$R^7$ group;
or
form together with the bridging nitrogen atom an at least mono-cyclic, optionally at least mono-substituted, at least one heteroatom containing heterocyclyl group which is optionally condensed with an optionally at least mono-substituted mono- or polycyclic ring system and/or bonded via linear alkylen groups and/or is optionally bound through a spirocyclic binding to an optionally at least mono-substituted mono- or polycyclic ring system;
t is selected from 0, 1, 2 or 3;
$R^3$ represents a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system;

$R^4$ and $R^5$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

or form together a 3 to 6-membered, optionally at least mono-substituted ring system;

$R^6$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^7$ and $R^{7a}$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^8$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferably t is selected from 1, 2 or 3.

In one embodiment the following proviso applies:
with the proviso that
if $R^3$ is H, m and n are each 1, the dotted line ------ represents a single bond, $R^4$, $R^5$ and $R^6$ are hydrogen and $R^8$ is $CH_2OH$, $R^1$ and $R^2$ may not form together with the bridging nitrogen atom an unsubstituted pyrrolidine.

In one embodiment the following proviso applies:
with the proviso that
if $R^3$ is H, m and n are each 1, the dotted line ------ represents a single bond, $R^4$, $R^5$ and $R^6$ are hydrogen and $R^8$ is C(O)H, $R^1$ and $R^2$ may not form together with the bridging nitrogen atom an unsubstituted pyrrolidine.

In one other embodiment the following proviso applies:
with the proviso that
if $R^3$ is H, m and n are each 1, the dotted line ------ represents a double bond, and $R^4$, $R^5$, $R^6$ and $R^8$ are hydrogen, $R^1$ and $R^2$ may not form together with the bridging nitrogen atom an unsubstituted pyrrolidine.

In one other embodiment the following proviso applies:
with the proviso that
if $R^3$ is H, m and n are each 1, $R^4$, $R^5$, $R^6$ are hydrogen, the dotted line ------ represents a single bond, and $R^1$ and $R^2$ form together with the bridging nitrogen atom an unsubstituted pyrrolidine, $R^8$ may not be CH=Het, with Het being a phenyl-substituted 1,3-dihydro-indol-2-one.

In one other embodiment the following proviso applies:
with the proviso that
if $R^3$ is H, m is 1, n is 0, $R^4$, $R^5$, $R^6$ and $R^8$ are hydrogen, and the dotted line ------ represents a double bond, one of $R^1$ or $R^2$ may not be hydrogen, when the other is C(O)-cyclohexyl.

In one other embodiment the following proviso applies:
with the provisos that
if $R^3$ is H, m and n are each 1, the dotted line ------ represents a single bond, $R^4$, $R^5$ and $R^6$ are hydrogen and $R^8$ is $CH_2OH$, $R^1$ and $R^2$ may not form together with the bridging nitrogen atom an unsubstituted pyrrolidine;
if $R^3$ is H, m and n are each 1, the dotted line ------ represents a single bond, and $R^4$, $R^5$, $R^6$ and $R^8$ are hydrogen, $R^1$ and $R^2$ may not form together with the bridging nitrogen atom an unsubstituted pyrrolidine;
if $R^3$ is H, m and n are each 1, $R^4$, $R^5$, $R^6$ are hydrogen, the dotted line ------ represents a single bond, and $R^1$ and $R^2$ form together with the bridging nitrogen atom an unsubstituted pyrrolidine, $R^8$ may not be CH=Het, with Het being a phenyl-substituted 1,3-dihydro-indol-2-one;

if $R^3$ is H, m is 1, n is 0, $R^4$, $R^5$, $R^6$ and $R^8$ are hydrogen, and the dotted line ------ represents a double bond, one of $R^1$ or $R^2$ may not be hydrogen, when the other is C(O)-cyclohexyl.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

In the context of this invention, alkyl radical or group is understood as meaning saturated and unsaturated, linear or branched hydrocarbons, which can be unsubstituted or mono- or polysubstituted. Thus unsaturated alkyl is understood to encompass alkenyl and alkinyl groups, like e.g. —CH=CH—$CH_3$ or —C≡C—$CH_3$, while saturated alkyl encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In the context of this invention aliphatic group or radical includes alkyl (saturated), alkenyl (unsaturated alkyl) and alkinyl (unsaturated alkyl) and thus is synonymous for: saturated or unsaturated alkyl (see above).

In the context of this invention cycloalkyl radical or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. However, mono- or polyunsaturated, preferably monounsaturated, cycloalkyls also in particular fall under the term cycloalkyl as long as the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantly.

In the context of this invention alkyl-cycloalkyl is understood as meaning a cycloalkyl group (see above) being connected to another atom through an alkyl group (see above), whereas the alkyl is always saturated and linear or branched always refers to the alkyl.

In connection with alkyl or aliphatic group—unless defined otherwise—the term substituted in the context of this invention is understood as meaning replacement of at least one hydrogen radical by F, Cl, Br, I, $NH_2$, SH or OH, "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH=CH—$CHCl_2$.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

An aryl radical or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

In the context of this invention alkyl-aryl is understood as meaning an aryl group (see above) being connected to another atom through an alkyl-group (see above), whereas the alkyl is always saturated and linear or branched always refers to the alkyl.

A heterocyclyl radical or group is understood as meaning heterocyclic ring systems, saturated or unsaturated ring which contains one or more heteroatoms from the group consisting of nitrogen, oxygen and/or sulfur in the ring and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline.

In the context of this invention alkyl-heterocyclyl is understood as meaning a heterocyclyl group (see above) being connected to another atom through an alkyl group (see above), whereas the alkyl is always saturated and linear or branched always refers to the alkyl.

In connection with aryl or alkyl-aryl, cycloalkyl or alkyl-cycloalkyl, heterocyclyl or alkyl-heterocyclyl, substituted is understood—unless defined otherwise—as meaning substitution of the ring-system of the aryl or alkyl-aryl, cycloalkyl or alkyl-cycloalkyl; heterocyclyl or alkyl-heterocyclyl by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—C$_{1-6}$-alkyl-group; a saturated or unsaturated, linear or branched, substituted or unsubstituted —C(O)—O—C$_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl.

The term "ring system" according to the present invention refers to ring systems comprising saturated or unsaturated or aromatic carbocyclic ring systems which contain optionally at least one heteroatom selected from N, O or S as ring member and which are optionally at least mono-substituted. Said ring systems may be condensed to other carbocyclic ring systems such as aryl groups, heterocyclyl groups, cycloalkyl groups, etc.

The term "condensed" according to the present invention means that a ring or ring-system is attached to another ring or ring-system, whereby the terms "annulated" or "annelated" are also used by those skilled in the art to designate this kind of attachment.

The term "bound through a spirocyclic binding to an optionally at least mono-substituted mono- or polycyclic ring system" means a binding through one C-Atom between two ring systems, like e.g. in below structure where the spirocyclic binding is marked by an arrow:

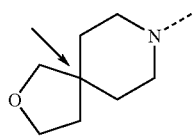

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid— as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts, solvates or prodrugs.

The term "pharmacological tool" refers to the property of compounds of the invention through which they are particularly selective ligands for Sigma receptors which implies that compound of formula (I), described in this invention, can be used as a model for testing other compounds as sigma ligands, ex. a radiactive ligands being replaced, and can also be used for modeling physiological actions related to sigma receptors.

Preferred are compounds of general formula (I) given above,
wherein
A represents a NR$^3$ group or O;
m is selected from 0, 1, 2;
n is selected from 0, 1, 2, 3, 4;
the dotted line ------ represents either a single or a double bond;
R$^1$ and R$^2$, identical or different, represent a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system; a (C=O)—$R^7$ group; a (C=O)—O—$R^7$ group; a (SO$_t$)—$R^7$ group; a $NR^7R^{7a}$ group; a (C=O)—$NR^7R^{7a}$ group; an O—$R^7$ group;

t is selected from 0, 1, 2, or 3;

or form together with the bridging nitrogen atom an at least mono-cyclic, optionally at least mono-substituted, at least one heteroatom containing heterocyclyl group which is optionally condensed with an optionally at least mono-substituted mono- or polycyclic ring system and/or bonded via linear alkylen groups and/or is optionally bound through a spirocyclic binding to an optionally at least mono-substituted mono- or polycyclic ring system;

$R^3$ represents a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system;

$R^4$ and $R^5$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$-alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^6$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^7$ and $R^{7a}$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^8$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferably t is selected from 0, 1, 2, or 3;

Also preferred are compounds according to the invention, wherein

A represents an $NR^3$ group;

m is selected from 0, 1, 2;

n is selected from 0, 1, 2, 3, 4;

the dotted line ------ represents either a single or a double bond;

$R^1$ and $R^2$, identical or different, represent a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system; a (C=O)—$R^7$ group; a (C=O)—O—$R^7$ group; a (SO$_t$)—$R^7$ group; a $NR^7R^{7a}$ group; a (C=O)—$NR^7R^{7a}$ group; an O—$R^7$ group;

t is selected from 0, 1, 2, or 3;

or form together with the bridging nitrogen atom an at least mono-cyclic, optionally at least mono-substituted, at least one heteroatom containing heterocyclyl group which is condensed and/or bonded via linear alkylen groups with an optionally at least mono-substituted mono- or polycyclic ring system and/or is optionally bound through a spirocyclic binding to an optionally at least mono-substituted mono- or polycyclic ring system;

$R^3$ represents a hydrogen atom; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems; an optionally at least mono-substituted aryl group which is optionally condensed to other, at least mono-substituted, mono- or polycyclic ring systems; an optionally at least mono-substituted heterocyclyl group which is optionally condensed to other, at least mono-substituted, mono- or polycyclic ring systems; a branched or unbranched, saturated or unsaturated, optionally at least mono-substituted alkyl-cycloalkyl group in which the cycloalkyl group may be optionally at least mono-substituted and/or condensed with a mono- or polycyclic ring system; a branched or unbranched, saturated, optionally at least mono-substituted alkyl-aryl group in which the aryl group may be optionally at least mono-substituted and/or condensed with a mono- or polycyclic ring system; a branched or unbranched, saturated, optionally at least mono-substituted alkyl-heterocyclyl group in which the heterocyclyl group may be optionally at least mono-substituted and/or condensed with a mono- or polycyclic ring system;

$R^4$ and $R^5$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^6$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^7$ and $R^{7a}$, identical or different, represent a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^8$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferably t is selected from 1, 2, or 3;

Preferred are also compounds of general formula (I) given above, wherein

A represents a $NR^3$ group or O;

m is selected from 0, 1, 2;

n is selected from 0, 1, 2, 3, 4;

the dotted line ------ represents either a single or a double bond;

$R^1$ and $R^2$, identical or different, represent a hydrogen atom; an unbranched or branched, substituted $C_{1-6}$ alkyl group with substituents independently selected from the group consisting of F, Cl, Br, I, $NH_2$, SH, OH, or $CF_3$; a saturated or unsaturated cycloalkyl group which is optionally at least mono-substituted with substituents independently selected from the group consisting of F, Cl, Br, I, $NH_2$, SH, OH, or $CF_3$; an aryl group which is optionally at least mono-substituted with substituents independently selected from the group consisting of F, Cl, Br, I, $NH_2$, SH, OH, or $CF_3$; a heterocyclyl group which is optionally at least mono-substituted with substituents independently selected from the group consisting of F, Cl, Br, I, $NH_2$, SH, OH, or $CF_3$; a branched or unbranched alkyl-cycloalkyl group in which the cycloalkyl group is optionally at least mono-substituted with substituents independently selected from the group consisting of F, Cl, Br, I, NH$_2$, SH, OH, or CF$_3$; a branched or unbranched alkyl-aryl group which is optionally at least mono-substituted with substituents independently selected from the group consisting of F, Cl, Br, I, NH$_2$, SH, OH, or CF$_3$; a branched or unbranched alkyl-heterocyclyl group which is optionally at least mono-substituted with substituents independently selected from the group consisting of F, Cl, Br, I, NH$_2$, SH, OH, or CF$_3$;

or form together with the bridging nitrogen atom an at least mono-cyclic, at least mono-substituted, at least one heteroatom containing heterocyclyl group selected from the group consisting of:

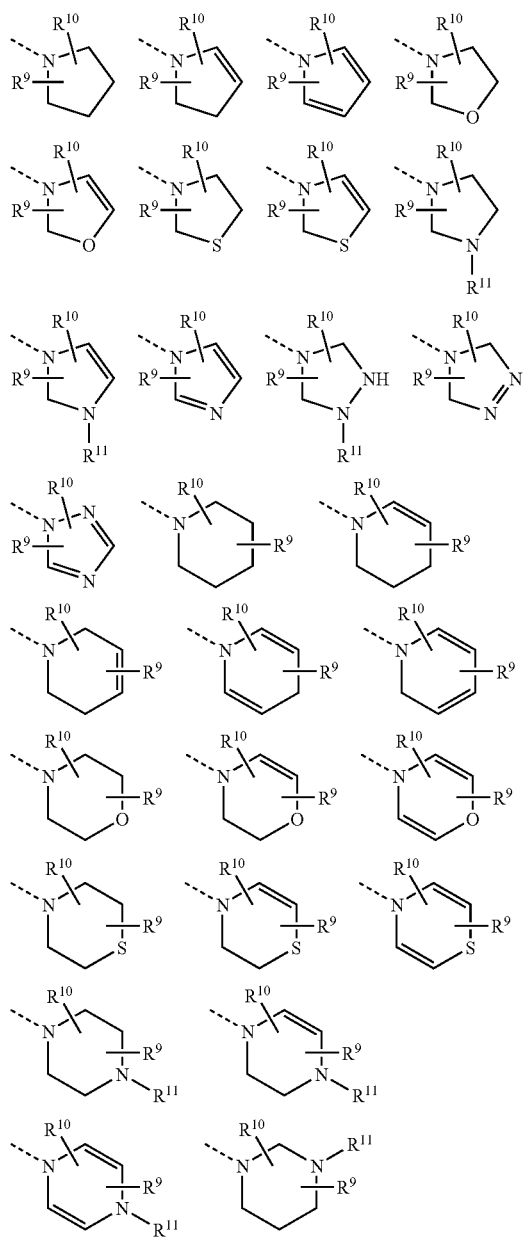

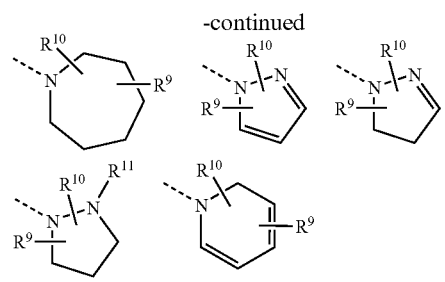

which is optionally condensed with an optionally at least mono-substituted mono- or polycyclic ring system; or which is optionally bound through a spirocyclic binding to an optionally at least mono-substituted mono- or polycyclic ring system;

R$^3$ represents a hydrogen atom; an unbranched or branched, substituted C$_{1-6}$ alkyl group with substituents independently selected from the group consisting of F, Cl, Br, I, NH$_2$, SH, OH, or CF$_3$; a saturated or unsaturated cycloalkyl group which is optionally at least mono-substituted with substituents independently selected from the group consisting of F, Cl, Br, I, NH$_2$, SH, OH, or CF$_3$; an aryl group which is optionally at least mono-substituted with substituents independently selected from the group consisting of F, Cl, Br, I, NH$_2$, SH, OH, or CF$_3$; a heterocyclyl group which is optionally at least mono-substituted with substituents independently selected from the group consisting of F, Cl, Br, I, NH$_2$, SH, OH, or CF$_3$; a branched or unbranched alkyl-cycloalkyl group in which the cycloalkyl group is optionally at least mono-substituted with substituents independently selected from the group consisting of F, Cl, Br, I, NH$_2$, SH, OH, or CF$_3$; a branched or unbranched alkyl-aryl group which is optionally at least mono-substituted with substituents independently selected from the group consisting of F, Cl, Br, I, NH$_2$, SH, OH, or CF$_3$; a branched or unbranched alkyl-heterocyclyl group which is optionally at least mono-substituted with substituents independently selected from the group consisting of F, Cl, Br, I, NH$_2$, SH, OH, or CF$_3$;

R$^4$ and R$^5$, identical or different, represent a hydrogen atom; F; Cl; Br; I; CF$_3$; OH; CN; an unbranched or branched, substituted C$_{1-6}$ alkyl group with substituents independently selected from the group consisting of F, Cl, Br, I, NH$_2$, SH, OH, or CF$_3$; an optionally, at least mono-substituted C$_{1-6}$ alkoxy group; a saturated or unsaturated cycloalkyl group which is optionally at least mono-substituted with substituents independently selected from the group consisting of F, Cl, Br, I, NH$_2$, SH, OH, or CF$_3$; an aryl group which is optionally at least mono-substituted with substituents independently selected from the group consisting of F, Cl, Br, I, NH$_2$, SH, OH, or CF$_3$; a heterocyclyl group which is optionally at least mono-substituted with substituents independently selected from the group consisting of F, Cl, Br, I, NH$_2$, SH, OH, or CF$_3$; a branched or unbranched alkyl-cycloalkyl group in which the cycloalkyl group is optionally at least mono-substituted with substituents independently selected from the group consisting of F, Cl, Br, I, NH$_2$, SH, OH, or CF$_3$; a branched or unbranched alkyl-aryl group which is optionally at least mono-substituted with substituents independently selected from the group consisting of F, Cl, Br, I, NH$_2$, SH, OH, or CF$_3$; a branched or unbranched alkyl-heterocyclyl group which is optionally at least mono-substituted with substituents independently selected from the group consisting of F, Cl, Br, I, $NH_2$, SH, OH, or $CF_3$;

$R^6$ represents a hydrogen atom; F; Cl; Br; I; $CF_3$; OH; CN; an unbranched or branched, substituted $C_{1-6}$ alkyl group with substituents independently selected from the group consisting of F, Cl, Br, I, $NH_2$, SH, OH, or $CF_3$; an optionally, at least mono-substituted $C_{1-6}$ alkoxy group; a saturated or unsaturated cycloalkyl group which is optionally at least mono-substituted with substituents independently selected from the group consisting of F, Cl, Br, I, $NH_2$, SH, OH or $CF_3$; an aryl group which is optionally at least mono-substituted with substituents independently selected from the group consisting of F, Cl, Br, I, $NH_2$, SH, OH or $CF_3$; a heterocyclyl group which is optionally at least mono-substituted with substituents independently selected from the group consisting of F, Cl, Br, I, $NH_2$, SH, OH or $CF_3$; a branched or unbranched alkyl-cycloalkyl group in which the cycloalkyl group is optionally at least mono-substituted with substituents independently selected from the group consisting of F, Cl, Br, I, $NH_2$, SH, OH or $CF_3$; a branched or unbranched alkyl-aryl group which is optionally at least mono-substituted with substituents independently selected from the group consisting of F, Cl, Br, I, $NH_2$, SH, OH or $CF_3$; a branched or unbranched alkyl-heterocyclyl group which is optionally at least mono-substituted with substituents independently selected from the group consisting of F, Cl, Br, I, $NH_2$, SH, OH or $CF_3$;

$R^7$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^8$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^9$ and $R^{10}$, identical or different, represents a hydrogen atom; a halogen; an $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^9$ and $R^{10}$, binding to the same ring-member, form together with this ring-member an optionally at least mono-substituted mono- or polycyclic ring system;

or $R^9$ and $R^{10}$, binding to different neighbouring ring members; form together with these ring members an optionally at least mono-substituted mono- or polycyclic ring system;

$R^{11}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula (I) given above, wherein

A represents an $NR^3$ group;

m is selected from 0, 1, 2;

n is selected from 0, 1, 2, 3, 4;

the dotted line ------ represents either a single or a double bond;

$R^1$ and $R^2$, identical or different, represent a hydrogen atom; an unbranched or branched, substituted $C_{1-6}$ alkyl group with substituents independently selected from the group consisting of F, Cl, Br, I, $NH_2$, SH, OH, or $CF_3$; a saturated or unsaturated cycloalkyl group which is optionally at least mono-substituted with substituents independently selected from the group consisting of F, Cl, Br, I, $NH_2$, SH, OH, or $CF_3$; an aryl group which is optionally at least mono-substituted with substituents independently selected from the group consisting of F, Cl, Br, I, $NH_2$, SH, OH, or $CF_3$; a heterocyclyl group which is optionally at least mono-substituted with substituents independently selected from the group consisting of F, Cl, Br, I, $NH_2$, SH, OH, or $CF_3$; a branched or unbranched alkyl-cycloalkyl group in which the cycloalkyl group is optionally at least mono-substituted with substituents independently selected from the group consisting of F, Cl, Br, I, $NH_2$, SH, OH, or $CF_3$; a branched or unbranched alkyl-aryl group which is optionally at least mono-substituted with substituents independently selected from the group consisting of F, Cl, Br, I, $NH_2$, SH, OH, or $CF_3$; a branched or unbranched alkyl-heterocyclyl group which is optionally at least mono-substituted with substituents independently selected from the group consisting of F, Cl, Br, I, $NH_2$, SH, OH, or $CF_3$;

or form together with the bridging nitrogen atom an at least mono-cyclic, at least mono-substituted, at least one het eroatom containing heterocyclyl group selected from the group consisting of:

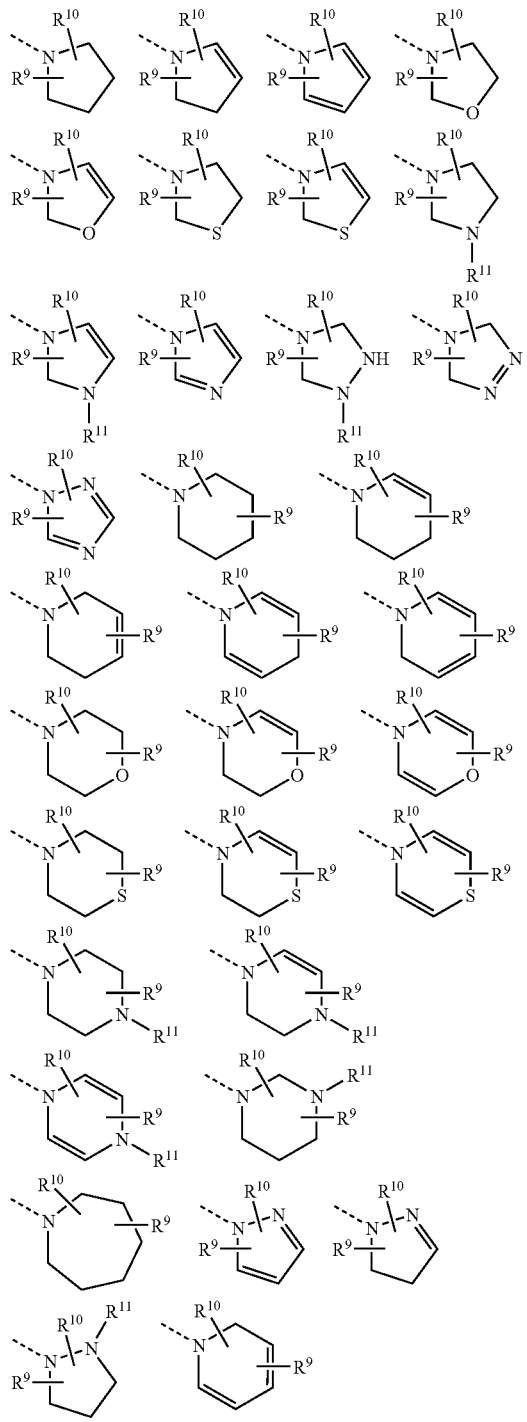

which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; an unbranched or branched, substituted $C_{1-6}$ alkyl group with substituents independently selected from the group consisting of F, Cl, Br, I, $NH_2$, SH, OH, or $CF_3$; a saturated or unsaturated cycloalkyl group which is optionally at least mono-substituted with substituents independently selected from the group consisting of F, Cl, Br, I, $NH_2$, SH, OH, or $CF_3$; an aryl group which is optionally at least mono-substituted with substituents independently selected from the group consisting of F, Cl, Br, I, $NH_2$, SH, OH, or $CF_3$; a heterocyclyl group which is optionally at least mono-substituted with substituents independently selected from the group consisting of F, Cl, Br, I, $NH_2$, SH, OH, or $CF_3$; a branched or unbranched alkyl-cycloalkyl group in which the cycloalkyl group is optionally at least mono-substituted with substituents independently selected from the group consisting of F, Cl, Br, I, $NH_2$, SH, OH, or $CF_3$; a branched or unbranched alkyl-aryl group which is optionally at least mono-substituted with substituents independently selected from the group consisting of F, Cl, Br, I, $NH_2$, SH, OH, or $CF_3$; a branched or unbranched alkyl-heterocyclyl group which is optionally at least mono-substituted with substituents independently selected from the group consisting of F, Cl, Br, I, $NH_2$, SH, OH, or $CF_3$;

$R^4$ and $R^5$, identical or different, represent a hydrogen atom; F; Cl; Br; I; $CF_3$; OH; CN; an unbranched or branched, substituted $C_{1-6}$ alkyl group with substituents independently selected from the group consisting of F, Cl, Br, I, $NH_2$, SH, OH, or $CF_3$; an optionally, at least mono-substituted $C_{1-6}$ alkoxy group; a saturated or unsaturated cycloalkyl group which is optionally at least mono-substituted with substituents independently selected from the group consisting of F, Cl, Br, I, $NH_2$, SH, OH, or $CF_3$; an aryl group which is optionally at least mono-substituted with substituents independently selected from the group consisting of F, Cl, Br, I, $NH_2$, SH, OH, or $CF_3$; a heterocyclyl group which is optionally at least mono-substituted with substituents independently selected from the group consisting of F, Cl, Br, I, $NH_2$, SH, OH, or $CF_3$; a branched or unbranched alkyl-cycloalkyl group in which the cycloalkyl group is optionally at least mono-substituted with substituents independently selected from the group consisting of F, Cl, Br, I, $NH_2$, SH, OH, or $CF_3$; a branched or unbranched alkyl-aryl group which is optionally at least mono-substituted with substituents independently selected from the group consisting of F, Cl, Br, I, $NH_2$, SH, OH, or $CF_3$; a branched or unbranched alkyl-heterocyclyl group which is optionally at least mono-substituted with substituents independently selected from the group consisting of F, Cl, Br, I, $NH_2$, SH, OH, or $CF_3$;

$R^6$ represents a hydrogen atom; F; Cl; Br; I; $CF_3$; OH; CN; an unbranched or branched, substituted $C_{1-6}$ alkyl group with substituents independently selected from the group consisting of F, Cl, Br, I, $NH_2$, SH, OH, or $CF_3$; an optionally, at least mono-substituted $C_{1-6}$ alkoxy group; a saturated or unsaturated cycloalkyl group which is optionally at least mono-substituted with substituents independently selected from the group consisting of F, Cl, Br, I, $NH_2$, SH, OH or $CF_3$; an aryl group which is optionally at least mono-substituted with substituents independently selected from the group consisting of F, Cl, Br, I, $NH_2$, SH, OH or $CF_3$; a heterocyclyl group which is optionally at least mono-substituted with substituents independently selected from the group consisting of F, Cl, Br, I, $NH_2$, SH, OH or $CF_3$; a branched or unbranched alkyl-cycloalkyl group in which the cycloalkyl group is optionally at least mono-substituted with substituents independently selected from the group consisting of F, Cl, Br, I, $NH_2$, SH, OH or $CF_3$; a branched or unbranched alkyl-aryl group which is optionally at least mono-substituted with substituents independently selected from the group consisting of F, Cl, Br, I, $NH_2$, SH, OH or $CF_3$; a branched or unbranched alkyl-heterocyclyl group which is optionally at least mono-substituted with substituents independently selected from the group consisting of F, Cl, Br, I, $NH_2$, SH, OH or $CF_3$;

$R^7$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^8$ represents a hydrogen atom; F; Cl; Br; I; $CF_3$; OH; CN; a linear or branched, saturated or unsaturated, optionally at least mono-substituted aliphatic radical; an optionally, at least mono-substituted $C_{1-6}$ alkoxy group; an optionally at least mono-substituted cycloalkyl group; an optionally at least mono-substituted aryl group; an optionally at least mono-substituted heterocyclyl group; a branched or unbranched, saturated or unsaturated, optionally at least mono-substituted alkyl-cycloalkyl group; a branched or unbranched, saturated, optionally at least mono-substituted alkyl-aryl group; a branched or unbranched, saturated, optionally at least mono-substituted alkyl-heterocyclyl group;

$R^9$ and $R^{10}$, identical or different, represents a hydrogen atom; a halogen; an $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^9$ and $R^{10}$, binding to the same ring-member, form together with this ring-member an optionally at least mono-substituted mono- or polycyclic ring system;

or $R^9$ and $R^{10}$, binding to different neighbouring ring members; form together with these ring members an optionally at least mono-substituted mono- or polycyclic ring system;

$R^{11}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula (I) given above, wherein $R^1$ and $R^2$ identical or different, represent a hydrogen atom; an unbranched or branched, substituted $C_{1-6}$ alkyl group with substituents independently selected from the group consisting of F, Cl, Br, I, $NH_2$, SH, OH, or $CF_3$; a saturated or unsaturated cycloalkyl group which is optionally at least mono-substituted with substituents independently selected from the group consisting of F, Cl, Br, I, $NH_2$, SH, OH, or $CF_3$; an aryl group which is optionally at least mono-substituted with substituents independently selected from the group consisting of F, Cl, Br, I, $NH_2$, SH, OH, or $CF_3$; a heterocyclyl group which is optionally at least mono-substituted with substituents independently selected from the group consisting of F, Cl, Br, I, $NH_2$, SH, OH, or $CF_3$; a branched or unbranched alkyl-cycloalkyl group in which the cycloalkyl group is optionally at least mono-substituted with substituents independently selected from the group consisting of F, Cl, Br, I, $NH_2$, SH, OH, or $CF_3$; a branched or unbranched alkyl-aryl group which is optionally at least mono-substituted with substituents independently selected from the group consisting of F, Cl, Br, I, $NH_2$, SH, OH, or $CF_3$; a branched or unbranched alkyl-heterocyclyl group which is optionally at least mono-substituted with substituents independently selected from the group consisting of F, Cl, Br, I, $NH_2$, SH, OH, or $CF_3$;

or form together with the bridging nitrogen atom an at least mono-cyclic, at least mono-substituted, at least one heteroatom containing heterocyclyl group preferably selected from the group consisting of:

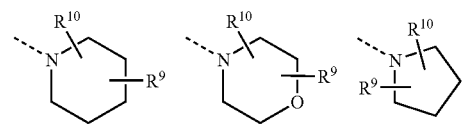

$R^7$ has the meaning given above;

$R^9$ and $R^{10}$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical selected from the group consisting of phenyl or naphtyl; an optionally at least mono-substituted heterocyclyl group preferably selected from the group consisting of:

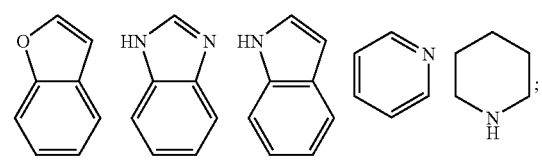

a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or

R$^9$ and R$^{10}$, binding to the same ring-member, form together with this ring-member an optionally at least mono-substituted spiro ring system which is preferably in meta-, ortho- or para-position;

or

R$^9$ and R$^{10}$, binding to different neighbouring ring members; form together with these ring members an optionally at least mono-substituted mono- or polycyclic ring system;

Preferred are also compounds of general formula (I) given above, wherein

R$^1$ and R$^2$ form together with the bridging nitrogen atom an at least mono-cyclic, at least mono-substituted, at least one heteroatom containing heterocyclyl group selected from the group consisting of:

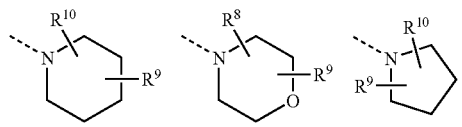

and R$^9$ and R$^{10}$, identical or different, are independently selected from the group consisting of: hydrogen, OH, F, Cl, Br, I, CN, NH$_2$, CF$_3$, CH$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H, oxo; an optionally at least mono-substituted benzyl group, an optionally at least mono-substituted phenyl group, an optionally at least mono-substituted naphtyl group, an optionally at least mono-substituted benzofuran group; an optionally at least mono-substituted benzoimidazole group; an optionally at least mono-substituted indole group; an optionally at least mono-substituted pyridine group.

and R$^9$ and R$^{10}$ are preferably in para-, meta-, or ortho-position.

Preferred are also compounds of general formula (I) given above, wherein

R$^9$ and R$^{10}$ form together with the bridging nitrogen atom an at least mono-substituted, spiro compound, which is optionally oxo-substituted and/or is optionally binding to different neighbouring ring members; form together with these ring members an optionally at least mono-substituted mono- or polycyclic ring system, and R$^9$ and R$^{10}$ are preferably in para-, meta-, or ortho-position.

Preferred are also compounds of general formula (I) given above, wherein m is selected from 0 or 1, preferably 1.

Preferred are also compounds of general formula (I) given above, wherein

A represents a NR$^3$ group or O;

m is selected from 1;

n is selected from 1, 2;

the dotted line ------ represents a single bond;

R$^1$ and R$^2$, identical or different, represent a hydrogen atom; an unbranched or branched, substituted C$_{1-6}$ alkyl group selected from the group consisting of methyl, ethyl, propyl, butyl, with substituents independently selected from the group consisting of F, Cl, Br, I, NH$_2$, SH, OH or CF$_3$; a branched or unbranched alkyl-aryl group, preferably benzyl or phenethyl, which is optionally at least mono-substituted with substituents independently selected from the group consisting of F, Cl, Br, I, NH$_2$, SH, OH, or CF$_3$;

or form together with the bridging nitrogen atom a heterocyclic group heterocyclyl group selected from the group consisting of:

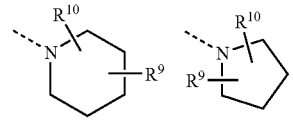

R$^3$ represents a hydrogen atom; methyl, ethyl, propyl, phenyl, benzyl, phenethyl, cyclopentyl, cyclohexyl, which are optionally at least mono-substituted with substituents independently selected from the group consisting of F, Cl, Br, I, NH$_2$, SH, OH or CF$_3$;

R$^4$ and R$^5$, identical or different, represent a hydrogen atom; F; Cl; Br; I; CF$_3$; OH; CN; methyl, ethyl, propyl, phenyl, benzyl, phenethyl, cyclopentyl, cyclohexyl, methoxy, ethoxy, which are optionally at least mono-substituted with substituents independently selected from the group consisting of F, Cl, Br, I, NH$_2$, SH, OH or CF$_3$;

R$^6$ represents a hydrogen atom; F; Cl; Br; I; CF$_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, NH$_2$, SH, OH or CF$_3$;

R$^8$ represents a hydrogen atom; F; Cl; Br; I; CF$_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, NH$_2$, SH, OH or CF$_3$;

R$^9$ and R$^{10}$, identical or different, are independently selected from the group consisting of: hydrogen, OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; an optionally at least mono-substituted benzyl group with substituents in ortho- meta- or para-position, independently selected from OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; an optionally at least mono-substituted phenyl group with substituents in ortho- meta- or para-position, independently selected from OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; a naphtyl group; a benzofuran group; a benzoimidazole group; an indole group; a pyridine group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula (I) given above, wherein m is selected from 0 or 1, preferably 1.

Preferred are also compounds of general formula (I) given above, wherein
A represents a NR³ group;
m is selected from 1;
n is selected from 1, 2;
the dotted line ------ represents a single bond;
R¹ and R², identical or different, represent a hydrogen atom; an unbranched or branched, substituted $C_{1-6}$ alkyl group selected from the group consisting of methyl, ethyl, propyl, butyl, with substituents independently selected from the group consisting of F, Cl, Br, I, $NH_2$, SH, OH or $CF_3$; a branched or unbranched alkyl-aryl group, preferably benzyl or phenethyl, which is optionally at least mono-substituted with substituents independently selected from the group consisting of F, Cl, Br, I, $NH_2$, SH, OH, or $CF_3$;
or
form together with the bridging nitrogen atom a heterocyclic group heterocyclyl group selected from the group consisting of:

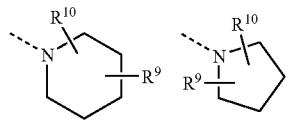

R³ represents a hydrogen atom; methyl, ethyl, propyl, phenyl, benzyl, phenethyl, cyclopentyl, cyclohexyl, which are optionally at least mono-substituted with substituents independently selected from the group consisting of F, Cl, Br, I, $NH_2$, SH, OH or $CF_3$;

R⁴ and R⁵, identical or different, represent a hydrogen atom; F; Cl; Br; I; $CF_3$; OH; CN; methyl, ethyl, propyl, phenyl, benzyl, phenethyl, cyclopentyl, cyclohexyl, methoxy, ethoxy, which are optionally at least mono-substituted with substituents independently selected from the group consisting of F, Cl, Br, I, $NH_2$, SH, OH or $CF_3$;

R⁶ represents a hydrogen atom; F; Cl; Br; I; $CF_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, $NH_2$, SH, OH or $CF_3$;

R⁸ represents a hydrogen atom; F; Cl; Br; I; $CF_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, $NH_2$, SH, OH or $CF_3$;

R⁹ and R¹⁰, identical or different, are independently selected from the group consisting of: hydrogen, OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; an optionally at least mono-substituted benzyl group with substituents in ortho- meta- or para-position, independently selected from OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; an optionally at least mono-substituted phenyl group with substituents in ortho- meta- or para-position, independently selected from OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; a naphtyl group; a benzofuran group; a benzoimidazole group; an indole group; a pyridine group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula (I) given above,
wherein
A represents a NR³ group or O;
m is selected from 1;
n is selected from 1, 2;
the dotted line ------ represents a single bond;
R¹ and R², identical or different, represent a hydrogen atom; an unbranched or branched, substituted $C_{1-6}$ alkyl group selected from the group consisting of methyl, ethyl, propyl, butyl, with substituents independently selected from the group consisting of F, Cl, Br, I, $NH_2$, SH, OH or $CF_3$; a branched or unbranched alkyl-aryl group, preferably benzyl or phenethyl, which is optionally at least mono-substituted with substituents independently selected from the group consisting of F, Cl, Br, I, $NH_2$, SH, OH, or $CF_3$;
or
form together with the bridging nitrogen atom heterocyclyl group preferably selected from the group consisting of:

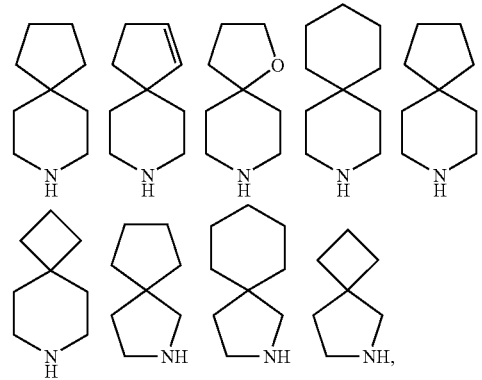

which is optionally oxo-substituted and/or is binding to different neighbouring ring members selected from the group consisting of an optionally at least mono-substituted aryl group;

R³ represents a hydrogen atom; methyl, ethyl, propyl, phenyl, benzyl, phenethyl, cyclopentyl, cyclohexyl, which are optionally at least mono-substituted with substituents independently selected from the group consisting of F, Cl, Br, I, $NH_2$, SH, OH or $CF_3$;

R⁴ and R⁵, identical or different, represent a hydrogen atom; F; Cl; Br; I; $CF_3$; OH; CN; methyl, ethyl, propyl, phenyl, benzyl, phenethyl, cyclopentyl, cyclohexyl, methoxy, ethoxy, which are optionally at least mono-substituted with substituents independently selected from the group consisting of F, Cl, Br, I, $NH_2$, SH, OH or $CF_3$;

R⁶ represents a hydrogen atom; F; Cl; Br; I; $CF_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, $NH_2$, SH, OH or $CF_3$;

$R^8$ represents a hydrogen atom; F; Cl; Br; I; $CF_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, $NH_2$, SH, OH or $CF_3$;

$R^9$ and $R^{10}$, identical or different, are independently selected from the group consisting of: hydrogen, OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; an optionally at least mono-substituted benzyl group with substituents in ortho- meta- or para-position, independently selected from OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; an optionally at least mono-substituted phenyl group with substituents in ortho- meta- or para-position, independently selected from OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; a naphtyl group; a benzofuran group; a benzoimidazole group; an indole group; a pyridine group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula (I) given above, wherein

A represents an $NR^3$ group;

m is selected from 1;

n is selected from 1, 2;

the dotted line ------ represents a single bond;

$R^1$ and $R^2$, identical or different, represent a hydrogen atom; an unbranched or branched, substituted $C_{1-6}$ alkyl group selected from the group consisting of methyl, ethyl, propyl, butyl, with substituents independently selected from the group consisting of F, Cl, Br, I, $NH_2$, SH, OH or $CF_3$; a branched or unbranched alkyl-aryl group, preferably benzyl or phenethyl, which is optionally at least mono-substituted with substituents independently selected from the group consisting of F, Cl, Br, I, $NH_2$, SH, OH, or $CF_3$;

or form together with the bridging nitrogen atom heterocyclyl group preferably selected from the group consisting of:

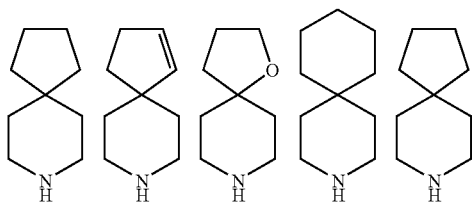

which is optionally oxo-substituted and/or is binding to different neighbouring ring members selected from the group consisting of an optionally at least mono-substituted aryl group;

$R^3$ represents a hydrogen atom; methyl, ethyl, propyl, phenyl, benzyl, phenethyl, cyclopentyl, cyclohexyl, which are optionally at least mono-substituted with substituents independently selected from the group consisting of F, Cl, Br, I, $NH_2$, SH, OH or $CF_3$;

$R^4$ and $R^5$, identical or different, represent a hydrogen atom; F; Cl; Br; I; $CF_3$; OH; CN; methyl, ethyl, propyl, phenyl, benzyl, phenethyl, cyclopentyl, cyclohexyl, methoxy, ethoxy, which are optionally at least mono-substituted with substituents independently selected from the group consisting of F, Cl, Br, I, $NH_2$, SH, OH or $CF_3$;

$R^6$ represents a hydrogen atom; F; Cl; Br; I; $CF_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, $NH_2$, SH, OH or $CF_3$;

$R^8$ represents a hydrogen atom; F; Cl; Br; I; $CF_3$; OH; CN; methyl, ethyl, propyl, phenyl, benzyl, phenethyl, cyclopentyl, cyclohexyl methoxy, ethoxy, which are optionally at least mono-substituted with substituents independently selected from the group consisting of F, Cl, Br, I, $NH_2$, SH, OH or $CF_3$;

$R^9$ and $R^{10}$, identical or different, are independently selected from the group consisting of: hydrogen, OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; an optionally at least mono-substituted benzyl group with substituents in ortho- meta- or para-position, independently selected from OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; an optionally at least mono-substituted phenyl group with substituents in ortho- meta- or para-position, independently selected from OH, F, Cl, Br, I, CN, $NH_2$, $CF_3$, O-Methyl, O-Ethyl, O-propyl, O-butyl, S-Methyl, S-Ethyl, S-propyl, O—$CH_3$, $C_{1-4}$-alkyl, (CO)—O-Methyl, $CO_2H$; a naphtyl group; a benzofuran group; a benzoimidazole group; an indole group; a pyridine group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula (I) given above, wherein

A represents an $NR^3$ group;

m is selected from 1;

n is selected from 1, 2;

the dotted line ------ represents a single bond;

R$^1$ and R$^2$, identical or different, represent a hydrogen atom; an unbranched or branched, substituted C$_{1-6}$ alkyl group selected from the group consisting of methyl, ethyl, propyl, butyl, with substituents independently selected from the group consisting of F, Cl, Br, I, NH$_2$, SH, OH or CF$_3$; a branched or unbranched alkyl-aryl group, preferably benzyl or phenethyl, which is optionally at least mono-substituted with substituents independently selected from the group consisting of F, Cl, Br, I, NH$_2$, SH, OH, or CF$_3$;

or form together with the bridging nitrogen atom a heterocyclic group heterocyclyl group selected from the group consisting of:

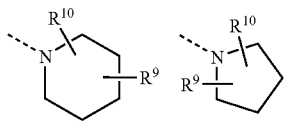

R$^3$ represents a hydrogen atom; methyl, ethyl, propyl, phenyl, benzyl, phenethyl, cyclopentyl, cyclohexyl, which are optionally at least mono-substituted with substituents independently selected from the group consisting of F, Cl, Br, I, NH$_2$, SH, OH or CF$_3$;

R$^4$ and R$^5$, identical or different, represent a hydrogen atom;

R$^6$ represents a hydrogen atom;

R$^8$ represents a hydrogen atom;

R$^9$ and R$^{10}$, identical or different, are independently selected from the group consisting of: hydrogen, OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; an optionally at least mono-substituted benzyl group with substituents in ortho- meta- or para-position, independently selected from OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; an optionally at least mono-substituted phenyl group with substituents in ortho- meta- or para-position, independently selected from OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; a naphtyl group; a benzofuran group; a benzoimidazole group; an indole group; a pyridine group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Preferred are also compounds of general formula (I) given above, wherein

A represents an NR$^3$ group;

m is selected from 1;

n is selected from 1, 2;

the dotted line ------ represents a single bond;

R$^1$ and R$^2$, identical or different, represent a hydrogen atom; an unbranched or branched, substituted C$_{1-6}$ alkyl group selected from the group consisting of methyl, ethyl, propyl, butyl, with substituents independently selected from the group consisting of F, Cl, Br, I, NH$_2$, SH, OH or CF$_3$; a branched or unbranched alkyl-aryl group, preferably benzyl or phenethyl, which is optionally at least mono-substituted with substituents independently selected from the group consisting of F, Cl, Br, I, NH$_2$, SH, OH, or CF$_3$;

or form together with the bridging nitrogen atom a heterocyclic group heterocyclyl group selected from the group consisting of:

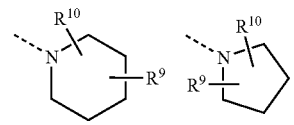

R$^3$ represents methyl, ethyl, propyl, phenyl, benzyl, phenethyl, cyclopentyl, cyclohexyl, which are optionally at least mono-substituted with substituents independently selected from the group consisting of F, Cl, Br, I, NH$_2$, SH, OH or CF$_3$;

R$^4$ and R$^5$, identical or different, represent a hydrogen atom;

R$^6$ represents a hydrogen atom;

R$^8$ represents a hydrogen atom;

R$^9$ and R$^{10}$, identical or different, are independently selected from the group consisting of: hydrogen, OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; an optionally at least mono-substituted benzyl group with substituents in ortho- meta- or para-position, independently selected from OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; an optionally at least mono-substituted phenyl group with substituents in ortho- meta- or para-position, independently selected from OH, F, Cl, Br, I, CN, NH$_2$, CF$_3$, O-Methyl, O-Ethyl, O-propyl, O-butyl, S-Methyl, S-Ethyl, S-propyl, O—CH$_3$, C$_{1-4}$-alkyl, (CO)—O-Methyl, CO$_2$H; a naphtyl group; a benzofuran group; a benzoimidazole group; an indole group; a pyridine group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Highly preferred are compounds of formula (I) given above, selected from the group consisting of:

N-benzyl-N-methyl-2-(1-methyl-4,5,6,7-tetrahydro-1H-indol-4-yl)ethanamine oxalate, 4-(4-chlorophenyl)-1-(2-(1-methyl-4,5,6,7-tetrahydro-1H-indol-4-yl)ethyl)piperidin-4-ol oxalate, 1-methyl-4-(2-(4-phenylpiperidin-1-yl)ethyl)-4,5,6,7-tetrahydro-1H-indole oxalate, N-benzyl-N-methyl-2-(1-methyl-4,5,6,7-tetrahydro-1H-indol-4-yl)ethanamine, 4-(4-chlorophenyl)-1-(2-(1-methyl-4,5,6,7-tetrahydro-1H-indol-4-yl)ethyl)piperidin-4-ol, 1-methyl-4-(2-(4-phenylpiperidin-1-yl)ethyl)-4,5,6,7-tetrahydro-1H-indole, optionally in form of one of the stereoisomers, preferably enantiomers or diastereomers, a racemate or in form of a mixture of at least two of the stereoisomers, preferably enantiomers and/or diastereomers, in any mixing ratio, or another corresponding salt thereof, or a corresponding solvate thereof.

Another aspect of the present invention relates to a process for the preparation of compounds of general formula (I) as described above.

Method A:

The compounds of formula (I) defined above can be obtained by available synthetic procedures. For example, they can be prepared according to the following scheme I:

Scheme I

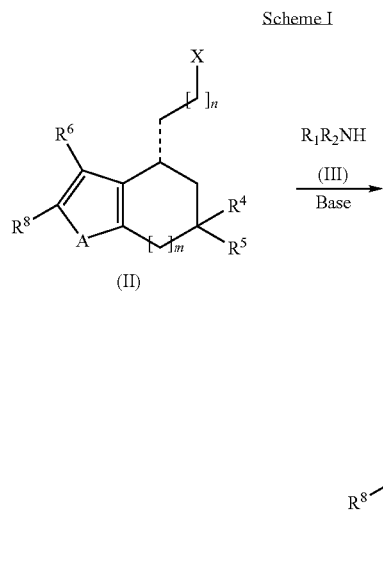

According to the Method A the compounds of formula (I) are prepared by coupling of a compound of Formula (II), in which A, $R^4$, $R^5$, $R^6$, m and n are as defined above in formula (I) and X is a leaving group, preferably chlorine or bromine with a compound of formula (III), $HNR^1R^2$, in which $R_1$ and $R_2$ are as defined above in formula (I).

The reaction of compounds of formula (II) and (III) is preferably carried out in an aprotic solvent, but not limited to, such as N,N-dimethylformamide (DMF) in the presence of an inorganic base, such as $K_2CO_3$, or an organic base, such as triethylamine or ethyldiisopropylamine, and at an appropriated temperature between room temperature and the reflux temperature of the solvent.

Compounds of formula (II) are also commercially available or can be prepared by methods well known in the literature. See, Berardi, F.; Giudice, G.; Perrone, R.; Tortorella, V.; Govoni, S.; Lucchi, L. *J. Med, Chem.* 1996, 39 4255-4260 and Christoph, J.; Frotscher, M.; Dannhardt, G.; Hartmann, R. *J. Med, Chem.* 2000, 43 1841-1851.

Method B:

The compounds of formula (I), as described above, can also be obtained according to the synthetic process described in scheme II:

Scheme II

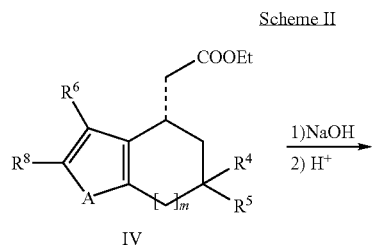

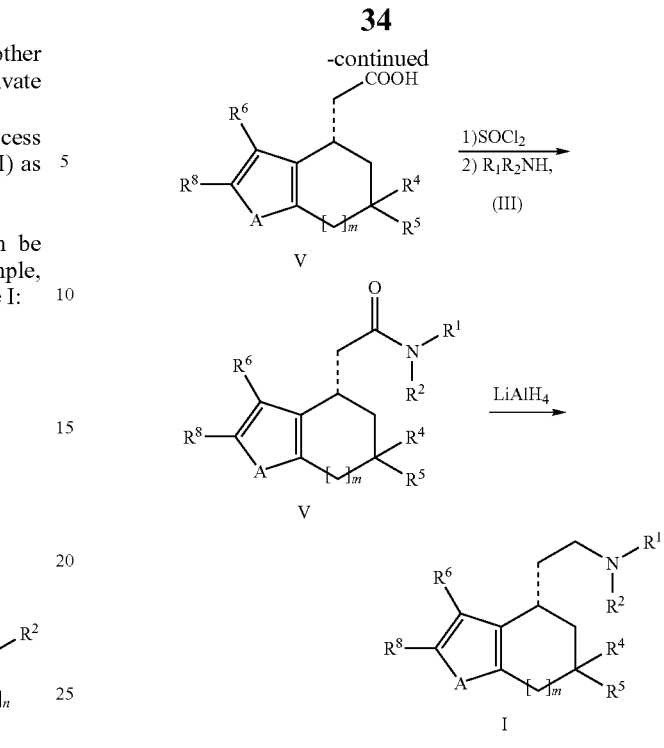

Following Method B, the compounds of formula (V) are prepared from the compounds of formula (IV) by hydrolysis of the ester group with a base such as NaOH, KOH or LiOH in a mixture of water and an alcohol such as methanol or ethanol, and at an appropriated temperature between room temperature and the reflux temperature of the solvent.

Following Method B, the compounds of formula (VI) are prepared by reaction of the compounds of formula (V) with thionyl chloride and subsequent treatment with amines of formula $R^1R^2NH$ (III) in an inert solvent such as methylene chloride at a temperature that can be between 0° C. and room temperature. The compounds of formula (VI) are prepared by reaction of the compounds of formula (V) with alkyl chloroformate, such as methyl chloroformate, ethyl chloroformate, isoprenyl chloroformate, or isobutyl chloroformate, in the presence of a base such as triethylamine, ethyldiisopropylamine or N-methylmorpholine, and subsequent treatment with amines of the formula $R^1R^2NH$ (III), in an inert solvent such as methylene chloride, tetrahydrofuran or N,N-dimethylformamide, and at an appropriated temperature between 0° C. and room temperature. The compounds of formula (VI) can also be prepared from the compounds of formula (V) and the amines of formula $R_1R_2NH$ (III) in the presence of reactives which activate carbonyl groups such as N,N'-dicyclohexylcarbodiimide, 1-(3-dimethylaminopropyl)-3-ethylcarbodiimide hydrochloride or diisopropylcarbodiimide. This reaction can also be carried out using the carbodiimides in the presence of 1-benzotriazole or N-hydroxysuccinimide. The compounds of formula (VI) can also be prepared from the compounds of formula (V) and the amines of formula $R^1R^2NH$ (III) in the presence of N,N'-carbonyldiimidazole.

Following Method B, the compounds of formula (I) are prepared from the compounds of formula (VI) by reaction with reducing agents such as lithium aluminum hydride.

During the processes described above the protection of sensitive groups or of reagents may be necessary and/or desirable. The introduction of conventional protective groups as well as their removal may be performed by methods well-known to those skilled in the art.

If the compounds of general formula (I) themselves are obtained in form of a mixture of stereoisomers, particularly enantiomers or diastereomers, said mixtures may be separated by standard procedures known to those skilled in the art, e.g. chromatographic methods or fractionalized crystallization with chiral reagents. If there are chiral centers the compounds may be prepared in racemic form, or individual enantiomers may be prepared either by enantiospecific synthesis or by resolution. Solvates, preferably hydrates, of the compounds of general formula (I), of corresponding stereoisomers, or of corresponding salts thereof may also be obtained by standard procedures known to those skilled in the art.

The purification and isolation of the inventive compounds of general formula (I), of a corresponding stereoisomer, or salt, or solvate or any intermediate thereof may, if required, be carried out by conventional methods known to those skilled in the art, e.g. chromatographic methods or recrystallization.

It has been found that the compounds of general formula (I) and given below, stereoisomers thereof, corresponding salts and corresponding solvates have high affinity to sigma receptors, i.e. they are selective ligands for the sigma receptor and act as modulators, e.g. antagonists, inverse agonists or agonists, on these receptors.

The compounds of general formula (I) given below, their stereoisomers, corresponding salts thereof and corresponding solvates are toxicologically acceptable and are therefore suitable as pharmaceutical active substances for the preparation of medicaments.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of the present invention relates to a medicament comprising at least one compound of general formula (I) given above, said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof; or a prodrug thereof.

In an alternative embodiment of the present invention, the medicament comprises at least one compound of general formula (I), said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another aspect of the invention is a medicament comprising at least one combination of compounds according to the invention and optionally one or more pharmaceutically acceptable excipients.

In an embodiment according to the invention the medicament is for the prophylaxis and/or treatment of one or more disorders selected from the group consisting of diarrhea, lipoprotein disorders, migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety or schizophrenia; inflammation, or autoimmune diseases.

In an embodiment according to the invention the medicament is for the prophylaxis and/or treatment of one or more disorders selected from the group consisting of elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and/or dysbetalipoproteinemia.

In another embodiment according to the invention the medicament is for the prophylaxis and/or treatment of one or more disorders selected from the group consisting of pain, preferably neuropathic pain, inflammatory pain or other pain conditions involving allodynia and/or hyperalgesia.

Said medicament may also comprise any combination of one or more of the compounds of general formula (I) given above, stereoisomers thereof, physiologically acceptable salts thereof or physiologically acceptable solvates thereof.

Another aspect of the present invention is the use of at least one compound of general formula (I) given above as suitable active substances, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, and optionally one or more pharmaceutically acceptable excipients, for the preparation of a medicament for the modulation of sigma receptors, preferably for the prophylaxis and/or treatment of psychosis.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Solid oral compositions (which are preferred as are liquid ones) may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to the methods well known in normal pharmaceutical practice, in particular with an enteric coating.

The mentioned formulations will be prepared using standard methods such as those described or referred to in the Spanish and US Pharmacopeias and similar reference texts.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Another aspect of the present invention refers to a method for the prophylaxis and/or treatment of diarrhea, lipoprotein disorders, migraine, obesity, elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and dysbetalipoproteinemia, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety or schizophrenia; inflammation, or autoimmune diseases, the method comprising administering to the subject at least one compound of general formula (I) as described above and optionally at least one further active substance and/or optionally at least one auxiliary substance to the subject.

A preferred embodiment of the present invention refers to a method for the prophylaxis and/or treatment of elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and/or dysbetalipoproteinemia.

The present invention is illustrated below with the aid of examples. These illustrations are given solely by way of example and do not limit the general spirit of the present invention.

EXAMPLES

Example 1

Synthesis of N-benzyl-N-methyl-2-(1-methyl-4,5,6,7-tetrahydro-1H-indol-4-yl)ethanamine Oxalate Step 1: Synthesis of ethyl 2-(1-methyl-4,5,6,7-tetrahydro-1H-indol-4-yl)acetate

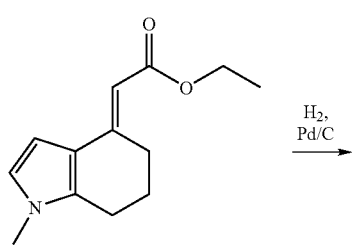

-continued

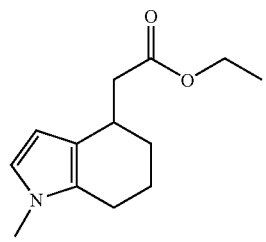

Pd—C (1.3 g, 5%) is added to a solution of a mixture of E/Z isomers of ethyl 2-(1-methyl-6,7-dihydro-1H-indol-4(5H)-ylidene)acetate (3.4 g, 15.50 mmoles) in 100 mL de EtOH, and the resulting solution is stirred under hydrogen atmosphere (25 psi) in a Parr hydrogenator for 8 hours. The reaction mixture is purged with nitrogen, filtered through Celite and the solvent is evaporated under reduced pressure to obtain ethyl 2-(1-methyl-4,5,6,7-tetrahydro-1H-indol-4-yl)acetate (3.4 g, 15.36 mmol, 99%, oil).

$^1$H NMR (300 MHz, CDCl$_3$): δ 1.28 (t, J=7.2 Hz, 3H), 1.39 (m, 1H), 1.75 (m, 1H), 1.94 (m, 2H), 2.32 (dd, J=14.9 Hz, J'=9.1 Hz, 1H), 2.49 (m, 2H), 2.68 (dd, J=14.9 Hz, J'=5.7 Hz, 1H), 3.15 (m, 1H), 3.46 (s, 3H), 4.17 (q, J=7.2 Hz, 2H), 5.93 (d, J=2.6 Hz, 1H), 6.48 (d, J=2.6 Hz, 1H).

Synthesis of 2-(1-methyl-4,5,6,7-tetrahydro-1H-indol-4-yl)ethanol

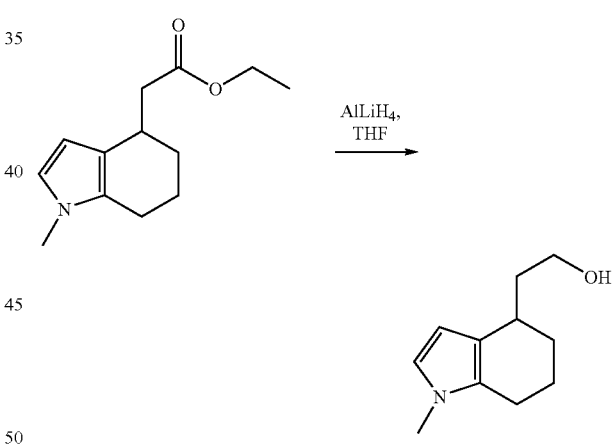

A solution of ethyl 2-(1-methyl-4,5,6,7-tetrahydro-1H-indol-4-yl)acetate (0.22 g, 1.00 mmol) in THF anh. is added slowly over a suspension of AlLiH$_4$ (0.1 g, 2.63 mmol) in THF anh. (10 mL) cooled in an ice bath. The mixture is maintained under stirring at room temperature for 1 hour and then is refluxed for 3 hours. The mixture is hydrolyzed with ice and NaOH (10%), filtered and the solvent is evaporated under reduced pressure. The residue is dissolved in ethyl acetate and washed with water. The organic phase is removed at reduced pressure and the resulting crude is purified by column chromatography, giving 2-(1-methyl-4,5,6,7-tetrahydro-1H-indol-4-yl)ethanol (0.15 g, 0.84 mmol, 84%, oil). $^1$H NMR (300 MHz, CDCl$_3$): δ 1.37 (m, 1H), 1.68 (m, 3H), 1.92 (m, 3H), 2.49 (m, 2H), 2.78 (m, 1H), 3.46 (s, 3H), 3.81 (m, 2H), 5.99 (d, J=2.5 Hz, 1H), 6.50 (d, J=2.5 Hz, 1H).

Synthesis of N-benzyl-N-methyl-2-(1-methyl-4,5,6,7-tetrahydro-1H-indol-4-yl)ethanamine Oxalate

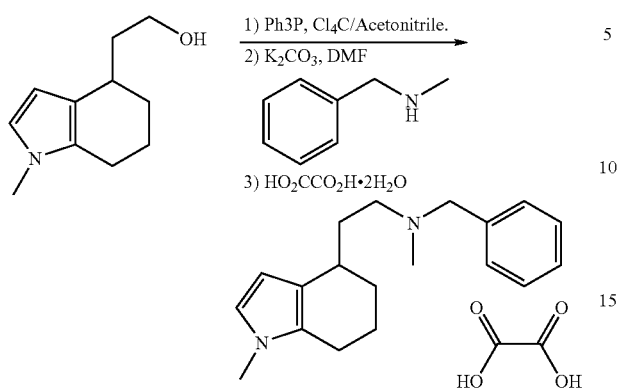

Triphenylphosphine (2.46 g, 9.38 mmol) is added to a solution of 2-(1-methyl-4,5,6,7-tetrahydro-1H-indol-4-yl)ethanol (1.68 g, 9.38 mmol) in $CCl_4$/Acetonitrile 1:1 (20 mL) at room temperature and the mixture is maintained under stirring for 3 hours monitoring the reaction by TLC. The solution is concentrated to half the volume at reduced pressure, $CH_2Cl_2$ is added and washed with water. The organic phase is separated and evaporated to dryness. The crude is treated with diethyl ether and the precipitated is filtered. The diethyl ether is evaporated at reduced pressure, and the resulting crude is purified by column chromatography, giving 4-(2-chloroethyl)-1-methyl-4,5,6,7-tetrahydro-1H-indole (0.8 g, 4.05 mmol, 43%, oil). (ESI-MS m/z 198 (M+H)$^+$.

A mixture of 4-(2-chloroethyl)-1-methyl-4,5,6,7-tetrahydro-1H-indole (0.1 g, 0.5 mmol), N-methyl-N-benzylamine (0.07 g, 0.5 mmol), $K_2CO_3$ (0.20 g, 1.45 mmol) and a catalytic amount of NaI in DMF (5 mL) is heated to 110° C. overnight. The solvent is removed at reduced pressure, diethyl ether is added to the residue and washed with water. The organic phase is dried and evaporated at reduced pressure and the resulting crude is purified by column chromatography, giving N-benzyl-N-methyl-2-(1-methyl-4,5,6,7-tetrahydro-1H-indol-4-yl)ethanamine (0.04 g, 0.14 mmol, 28%, oil). (ESI-MS m/z 283 (M+H)$^+$.

N-Benzyl-N-methyl-2-(1-methyl-4,5,6,7-tetrahydro-1H-indol-4-yl)ethanamine oxalate is prepared from a solution of N-benzyl-N-methyl-2-(1-methyl-4,5,6,7-tetrahydro-1H-indol-4-yl)ethanamine in acetone with a slightly excess of $HO_2CCO_2H.2H_2O$. Slightly pinkish solid. M.p.=123-125° C. $^1$H NMR (300 MHz, $CD_3OD$): δ 1.37 (m, 1H), 1.65-2.13 (m, 5H), 2.49 (m, 2H), 2.70 (m, 1H), 2.78 (s, 3H), 3.23 (m, 2H), 3.43 (s, 3H), 4.32 (m, 2H), 5.80 (d, J=2.8 Hz, 1H), 6.46 (d, J=2.8 Hz, 1H), 7.48 (s, 5H).

Example 2

4-(4-chlorophenyl)-1-(2-(1-methyl-4,5,6,7-tetrahydro-1H-indol-4-yl)ethyl)piperidin-4-ol

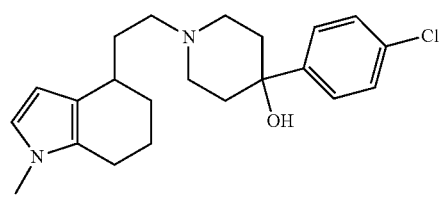 [SMILES: Cn1ccc2c1CCCC2CCN1CCC(O)(c2ccc(Cl)cc2)CC1]

$^1$H NMR (300 MHz, $CDCl_3$): δ 1.36 (m, 1H), 1.46-2.16 (m, 9H), 2.46-3.06 (m, 7H), 3.20 (m, 2H), 3.46 (s, 3H), 5.95 (d, J=2.6 Hz, 1H), 6.49 (d, J=2.6 Hz, 1H), 7.30 (d, J=8.6 Hz, 2H), 7.46 (d, J=8.6 Hz, 2H). (54%, oil).

Example 3

4-(4-chlorophenyl)-1-(2-(1-methyl-4,5,6,7-tetrahydro-1H-indol-4-yl)ethyl)piperidin-4-ol Oxalate

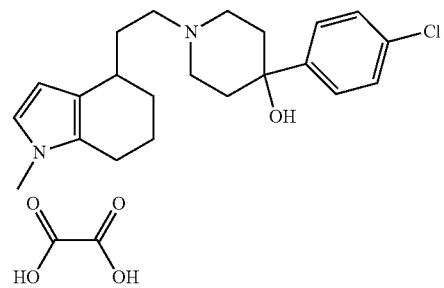

(m.p.=154-155° C., slightly pinkish solid).

Example 4

1-methyl-4-(2-(4-phenylpiperidin-1-yl)ethyl)-4,5,6,7-tetrahydro-1H-indole

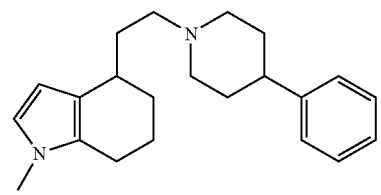 [SMILES: Cn1ccc2c1CCCC2CCN1CCC(c2ccccc2)CC1]

(5.8%, oil).

Example 5

1-methyl-4-(2-(4-phenylpiperidin-1-yl)ethyl)-4,5,6,7-tetrahydro-1H-indole Oxalate

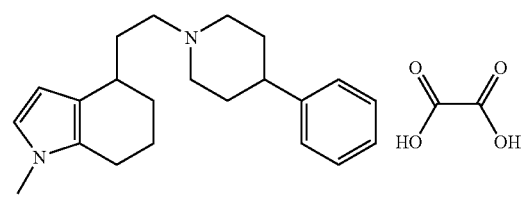

(m.p.=86-90° C., 75%, cream-colored solid).

Biological Activity

Some representative compounds of the invention are tested for their activity as sigma (sigma-1 and sigma-2) inhibitors. The following protocols are followed:

Sigma-1

Brain membrane preparation and binding assays for the σ1-receptor are performed as described (DeHaven-Hudkins et al., 1992) with some modifications. In brief, guinea pig brains are homogenized in 10 vols. (w/v) of Tris-HCl 50 mM 0.32 M sucrose, pH 7.4, with a Kinematica Polytron PT 3000 at 15000 r.p.m. for 30 s. The homogenate is centrifuged at 1000 g for 10 min at 4° C. and the supernatants collected and centrifuged again at 48000 g for 15 min at 4° C. The pellet is resuspended in 10 volumes of Tris-HCl buffer (50 mM, pH 7.4), incubated at 37° C. for 30 min, and centrifuged at 48000 g for 20 min at 4° C. Following this, the pellet is resuspended in fresh Tris-HCl buffer (50 mM, pH 7.4) and stored on ice until use.

Each assay tube contains 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding is defined by addition of a final concentration of 1 μM haloperidol. All tubes are incubated at 37° C. for 150 min before termination of the reaction by rapid filtration over Schleicher & Schuell GF 3362 glass fibre filters [previously soaked in a solution of 0.5% polyethylenimine for at least 1 h]. Filters are then washed four times with 4 mL of cold Tris-HCl buffer (50 mM, pH 7.4). Following addition of scintillation cocktail, the samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

Sigma-2

Binding studies for σ2-receptor are performed as described (Radesca et al., 1991) with some modifications. In brief, brains from sigma receptor type I (σ1) knockout mice are homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates are then centrifuged at 1000 g for 10 min at 4° C., and the supernatants are saved. The pellets are resuspended by vortexing in 2 mL/g ice-cold Tris-sucrose buffer and centrifuged again at 1000 g for 10 min. The combined 1000 g supernatants are centrifuged at 31000 g for 15 min at 4° C. The pellets are resuspended by vortexing in 3 mL/g 10 mM Tris-HCl, pH 7.4, and the suspension is kept at 25° C. for 15 min. Following centrifugation at 31000 g for 15 min, the pellets are resuspended by gentle Potter Elvehjem homogenization to a volume of 1.53 mL/g in 10 mM Tris-HCl pH 7.4.

The assay tubes contain 10 μL of [$^3$H]-DTG (final concentration of 3 nM), 400 μL of the tissue suspension (5.3 mL/g in 50 mM Tris-HCl, pH 8.0) to a final assay volume of 0.5 mL. Non-specific binding is defined by addition of a final concentration of 1 μM haloperidol. All tubes are incubated at 25° C. for 120 min before termination of the reaction by rapid filtration over Schleicher & Schuell GF 3362 glass fibre filters [previously soaked in a solution of 0.5% polyethylenimine for at least 1 h]. Filters are washed three times with 5 mL volumes of cold Tris-HCl buffer (10 mM, pH 8.0). Following addition of scintillation cocktail samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

REFERENCES

DeHaven-Hudkins, D. L., L. C. Fleissner, and F. Y. Ford-Rice, 1992, "Characterization of the binding of [$^3$H](+)pentazocine to σ recognition sites in guinea pig brain", Eur. J. Pharmacol. 227, 371-378.

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)cyclohexylamines as High-Affinity a Receptor Ligands, J. Med. Chem. 34, 3065-3074.

Langa, F., Codony X., Tovar V., Lavado A., Giménez E., Cozar P., Cantero M., Dordal A., Hernández E., Pérez R., Monroy X., Zamanillo D., Guitart X., Montoliu L I., 2003, Generation and phenotypic analysis of sigma receptor type I (Sigma1) knockout mice, European Journal of Neuroscience, Vol. 18, 2188-2196.

Lowry, O. H., N. J. Rosebrough, A. L. Farr, and R. J. Randall, 1951, Protein measurement with the Folin phenol reagent, J. Biol. Chem., 193, 265.

The invention claimed is:

1. Compounds of formula (I),

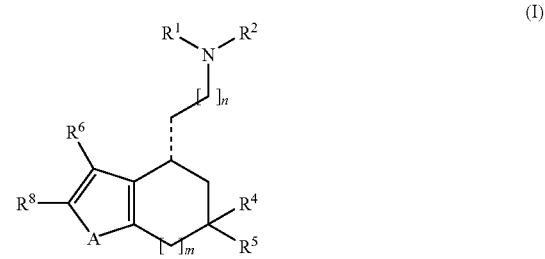

wherein

A represents an NR$^3$ group;

m is 1;

n is 1 or 2;

the dotted line ------ represents either a single or a double bond;

R$^1$ and R$^2$, identical or different, represent a hydrogen atom; an unbranched or branched, substituted C$_{1-6}$ alkyl group with substituents independently selected from the group consisting of F, Cl, Br, I, NH$_2$, SH, OH, and CF$_3$; a branched or unbranched alkyl-aryl group which is optionally at least mono-substituted with substituents independently selected from the group consisting of F, Cl, Br, I, NH$_2$, SH, OH, and CF$_3$;

or form together with the bridging nitrogen atom an at least mono-cyclic, at least mono-substituted, at least one heteroatom containing heterocyclyl group selected from the group consisting of:

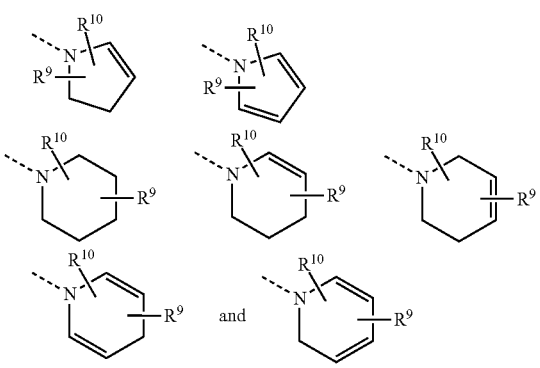

which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; an unbranched or branched, substituted $C_{1-6}$ alkyl group with substituents independently selected from the group consisting of F, Cl, Br, I, $NH_2$, SH, OH, and $CF_3$;

$R^4$ and $R^5$ represent a hydrogen atom;

$R^6$ represents a hydrogen atom;

$R^7$ represents a hydrogen atom;

$R^8$ represents a hydrogen atom;

$R^9$ and $R^{10}$, identical or different, represent a hydrogen atom; a halogen; $OR^7$; an optionally at least mono-substituted aryl radical selected from the group consisting of phenyl and naphtyl;

with the provisos that
if $R^3$ is H, m and n are each 1, the dotted line ------ represents a single bond, and $R^4$, $R^5$, $R^6$ and $R^8$ are hydrogen, $R^1$ and $R^2$ may not form together with the bridging nitrogen atom an unsubstituted pyrrolidine;

optionally in form of one of the stereoisomers, a racemate or in form of a mixture of at least two of the stereoisomers, in any mixing ratio, or a corresponding salt thereof.

2. The compounds according to claim 1, characterized in that
$R^1$ and $R^2$ form together with the bridging nitrogen atom an at least mono-cyclic, at least mono-substituted, at least one heteroatom containing a heterocyclyl group of:

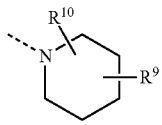

and
$R^9$ and $R^{10}$, identical or different, are independently selected from the group consisting of: hydrogen, OH, F, Cl, Br, I, an optionally at least mono-substituted benzyl group, an optionally at least mono-substituted phenyl group, and an optionally at least mono-substituted naphtyl group.

3. The compounds according to claim 2, characterized in that $R^9$ and $R^{10}$ are in para-, meta-, or ortho-position.

4. The compounds according to claim 1, characterized in that $R^9$ and $R^{10}$ are in para-, meta-, or ortho-position.

5. The compounds according to claim 1, wherein the compounds are selected from the group consisting of:
N-benzyl-N-methyl-2-(1-methyl-4,5,6,7-tetrahydro-1H-indol-4-yl)ethanamine oxalate,
4-(4-chlorophenyl)-1-(2-(1-methyl-4,5,6,7-tetrahydro-1H-indol-4-yl)ethyl)piperidin-4-ol oxalate,
1-methyl-4-(2-(4-phenylpiperidin-1-yl)ethyl)-4,5,6,7-tetrahydro-1H-indole oxalate,
N-benzyl-N-methyl-2-(1-methyl-4,5,6,7-tetrahydro-1H-indol-4-yl)ethanamine,
4-(4-chlorophenyl)-1-(2-(1-methyl-4,5,6,7-tetrahydro-1H-indol-4-yl)ethyl)piperidin-4-ol, and
1-methyl-4-(2-(4-phenylpiperidin-1-yl)ethyl)-4,5,6,7-tetrahydro-1H-indole, optionally in form of one of the stereoisomers, a racemate or in form of a mixture of at least two of the stereoisomers, in any mixing ratio, or another corresponding salt thereof.

6. A medicament comprising at least one compound of formula (I) according to claim 1, said compound being optionally in form of one of the stereoisomers, a racemate or in form of a mixture of at least two of the stereoisomers, in any mixing ratio, or a corresponding salt thereof, or a prodrug thereof.

7. The compounds according to claim 1, characterized in that
$R^1$ and $R^2$ form together with the bridging nitrogen atom an at least mono-cyclic, at least mono-substituted, at least one heteroatom containing a heterocyclyl group of:

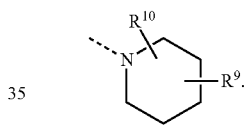

8. The compounds according to claim 1, characterized in that they are in the form of enantiomers or diastereomers, in any mixing ratio, or a corresponding salt thereof.

9. The compounds according to claim 5, characterized in that they are in the form of enantiomers or diastereomers, in any mixing ratio, or a corresponding salt thereof.

10. The medicament according to claim 6, characterized in that the at least one compound of formula (I) is in the form of enantiomers or diastereomers, in any mixing ratio, or a corresponding salt thereof.

* * * * *